(12) United States Patent
Berger et al.

(10) Patent No.: US 6,948,502 B2
(45) Date of Patent: Sep. 27, 2005

(54) METHOD AND APPARATUS FOR POSITIONING A FOREARM FOR IMAGING AND ANALYSIS

(75) Inventors: Richard A. Berger, Rochester, MN (US); Fredrick M. Schultz, Rochester, MN (US); Lawrence J. Berglund, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 559 days.

(21) Appl. No.: 10/142,331

(22) Filed: May 9, 2002

(65) Prior Publication Data

US 2003/0209248 A1 Nov. 13, 2003

(51) Int. Cl.[7] .............................................. A61G 15/00
(52) U.S. Cl. ...................... 128/845; 600/415; 600/427; 5/623
(58) Field of Search .............................. 128/845; 5/646, 5/647, 623, 621; 482/601, 45, 46, 114, 115; 601/33, 40; 600/427, 417, 415, 425, 429; 378/20, 177, 179, 180, 208, 204

(56) References Cited

U.S. PATENT DOCUMENTS

| | | | | |
|---|---|---|---|---|
| 2,819,081 | A | * | 1/1958 | Touraine ...................... 482/45 |
| 3,715,587 | A | * | 2/1973 | Burkhalter et al. ......... 378/195 |
| 4,181,297 | A | | 1/1980 | Nichols |
| 4,258,913 | A | * | 3/1981 | Brentham .................... 482/45 |
| 4,306,571 | A | | 12/1981 | McLeod, Jr. |
| 4,436,099 | A | | 3/1984 | Raftopoulos |
| 4,488,715 | A | | 12/1984 | Comeau |

(Continued)

OTHER PUBLICATIONS

Robert O. Cone, et al., "Computed Tomography of the Normal Radioulnar Joints," Investigative Radiology, 18(6):541–545, 1983.

Graham J. King, et al., "Computerized Tomography of the Distal Radioulnar Joint: Correlation with Ligamentous Pathology in a Cadaveric Model," The Journal of Hand Surgery, 11A(5):711–717, 1986.

David E. Mino, et al., "The Role of Radiography and Computerized Tomography in the Diagnosis of Subluxation and Dislocation of the Distal Radioulnar Joint," The Journal of Hand Surgery, 8(1):23–31. 1983.

David E. Mino, et al., "Radiography and Computerized Tomography in the Diagnosis of Incongruity of the Distal Radio–Ulnar Joint," The Journal of Bone and Joint Surgery, 67–A(2):247–252, 1985.

Ryogo Nakamura, et al., "Criteria for Diagnosing Distal Radioulnar Joint Subluxation by Computed Tomography," Skeletal Radiol. 25:649–653, 1996.

Arthur H. Newberg, "Computed Tomography of Joint Injuries," Orthopedics, 28(2):445–460, 1990.

(Continued)

*Primary Examiner*—Henry Bennett
*Assistant Examiner*—Camtu Nguyen
(74) *Attorney, Agent, or Firm*—Quarles & Brady LLP (57) ABSTRACT

Disclosed is a method and apparatus for repeatably positioning a forearm at a plurality of angular positions for medical analysis. A forearm of a patient is positioned in a support channel within reach of a rotatable handle. The handle can be locked in a number of angular positions, providing a counteractive force as the handle is rotated. The patient rotates and applies a torque force to the handle at selected rotational angles. The forearm and wrist can be scanned in these locked position, and applied torque can be measured to evaluate joint stability.

13 Claims, 6 Drawing Sheets

U.S. PATENT DOCUMENTS

| | | | |
|---|---|---|---|
| 4,549,555 A | 10/1985 | Fraser et al. | |
| 4,562,588 A | 12/1985 | Ruf | |
| 4,571,834 A | 2/1986 | Fraser et al. | |
| 4,583,555 A | 4/1986 | Malcom et al. | |
| 4,592,362 A | 6/1986 | Stedtfeld et al. | |
| 4,641,832 A * | 2/1987 | Mattox | 482/45 |
| 4,643,177 A | 2/1987 | Sheppard et al. | |
| 4,649,934 A | 3/1987 | Fraser et al. | |
| 4,674,110 A | 6/1987 | Eaton et al. | |
| 4,698,837 A | 10/1987 | Van Steenburg | |
| 4,799,497 A | 1/1989 | Riley, II | |
| 4,922,925 A | 5/1990 | Crandall et al. | |
| 5,082,001 A | 1/1992 | Vannier et al. | |
| 5,136,743 A | 8/1992 | Pirela-Cruz | |
| 5,323,786 A | 6/1994 | Juhasz | |
| 5,327,912 A | 7/1994 | Mally | |
| 5,391,132 A * | 2/1995 | Greenwald | 482/91 |
| 5,462,068 A | 10/1995 | Rijke et al. | |
| 5,485,856 A | 1/1996 | Buckland | |
| 5,487,395 A | 1/1996 | Strowe | |
| 5,513,651 A | 5/1996 | Cusimano et al. | |
| 5,657,369 A | 8/1997 | Stein et al. | |
| 5,662,121 A | 9/1997 | Zucker | |
| 5,676,622 A * | 10/1997 | McFarlane | 482/45 |
| 5,712,892 A * | 1/1998 | Weil et al. | 378/54 |
| 5,713,370 A * | 2/1998 | Cook | 600/595 |
| 5,724,991 A | 3/1998 | Rijke et al. | |
| 5,788,607 A * | 8/1998 | Baker | 482/44 |
| 5,881,730 A | 3/1999 | Burger | |
| 5,919,148 A | 7/1999 | Marko et al. | |
| 5,957,869 A | 9/1999 | Caruso et al. | |
| 5,961,474 A | 10/1999 | Reis | |
| 6,045,517 A | 4/2000 | Williams | |
| 6,315,701 B1 * | 11/2001 | Shifferaw | 482/114 |
| 6,676,570 B2 * | 1/2004 | Valentino | 482/45 |

OTHER PUBLICATIONS

Miguel A. Pirela–Cruz, et al., "Stress Computed Tomography Analysis of the Distal Radioulnar Joint: A Diagnostic Tool for Determining Translational Motion," The Journal of Hand Surgery, 16A(1):75–82, 1991.

Richard J. Wechsler, et al., "Computed Tomography Diagnosis of Distal Radioulnar Subluxation," Skeletal Radiol. 16:1–5, 1987.

Jack M. Winters and Douglas G. Kleweno, "Effect on Initial Upper–limb Alignment on Muscle Contributions to Isometric Strength Curves," J. Biomechanics, 26(2):143–153, 1993.

* cited by examiner

METHOD AND APPARATUS FOR POSITIONING A FOREARM FOR IMAGING AND ANALYSIS

The present invention is related to positioning devices for medically examining joints, and more particularly to a medical positioning device for positioning the forearm and wrist for DRUJ analysis.

BACKGROUND

Abnormalities of the proximal and distal radioulnar joints (DRUJ) are commonly encountered in clinical practice in association with trauma or dislocation, synovial inflammatory diseases, or congenital abnormalities and may be associated with numerous conditions, including ulnar styloid fracture, Colles fracture, radial diaphyseal fracture, radial head fracture or excision, triangular fibrocartilage complex injury, and disproportionate radioulnar length. The diagnosis of DRUJ abnormalities is difficult, however, since limitations of conventional radiologic imaging procedures make it difficult or impossible to radiographically confirm subluxation or dislocation of the DRUJ. Abnormalities of the DRUJ may, therefore, go undiagnosed.

Computed Tomography (CT), however, can be used to image the DRUJ. Since CT delineates the cross-sectional anatomy of the DRUJ, this technique can be utilized for the evaluation of the anatomy and mobility of the DRUJ, as well as for suspected joint subluxation. However, a number of problems have also been associated with attempts to diagnose abnormalities of the DRUJ using CT. First, prior art evaluation protocols do not provide a means for positioning the right and left upper extremity in a consistent fashion. Typically, the forearms are simply placed in the CT gantry with the wrists at approximately the same level, and the patient is asked to rotate the forearm into maximum pronation (palm down) and supination (palm up) positions. Thus, the wrists may be at different levels and the forearms may be at different degrees of rotation within the scan. Because the location of the forearms and wrists are not consistent, it is necessary to obtain a large number of images, in order to insure that the same regions of both wrists are imaged. Because of the large number of images acquired, the patients are exposed to a significant degree of radiation. Furthermore, when both forearms are not positioned in the same degree of rotation, it is not possible to compare a left and right wrist or forearm. Additionally, even though most patients complain of their most severe symptoms while actively using their upper extremities, prior art methods do not provide a means for simulating or generating resisted rotation.

There remains a need, therefore, for a method and apparatus for consistently positioning and rotating a forearm for purposes of imaging and evaluating the forearm joints.

SUMMARY OF THE INVENTION

The present invention is a method and apparatus for positioning the forearm of a subject for clinical examination. A support channel and a rotatable handle are coupled to a frame. The support channel is positioned on the frame along a longitudinal access, and is sized and dimensioned to receive the forearm of a subject. The rotatable axis is positioned at a location relative to the support channel such that the subject can grip and rotate the handle. Rotation of the handle is centered substantially around the longitudinal axis.

Another aspect of the invention comprises providing a counteractive force opposing the rotation of the rotatable handle. The subject is prompted to rotate the rotatable handle against the counteractive force to provide a torque on the handle. A torque cell can be used to measure the applied torque.

The foregoing and other aspects of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims herein for interpreting the scope of the invention.

DETAILED DESCRIPTION OF THE PREFERRED EMBODIMENT

Figure 1:
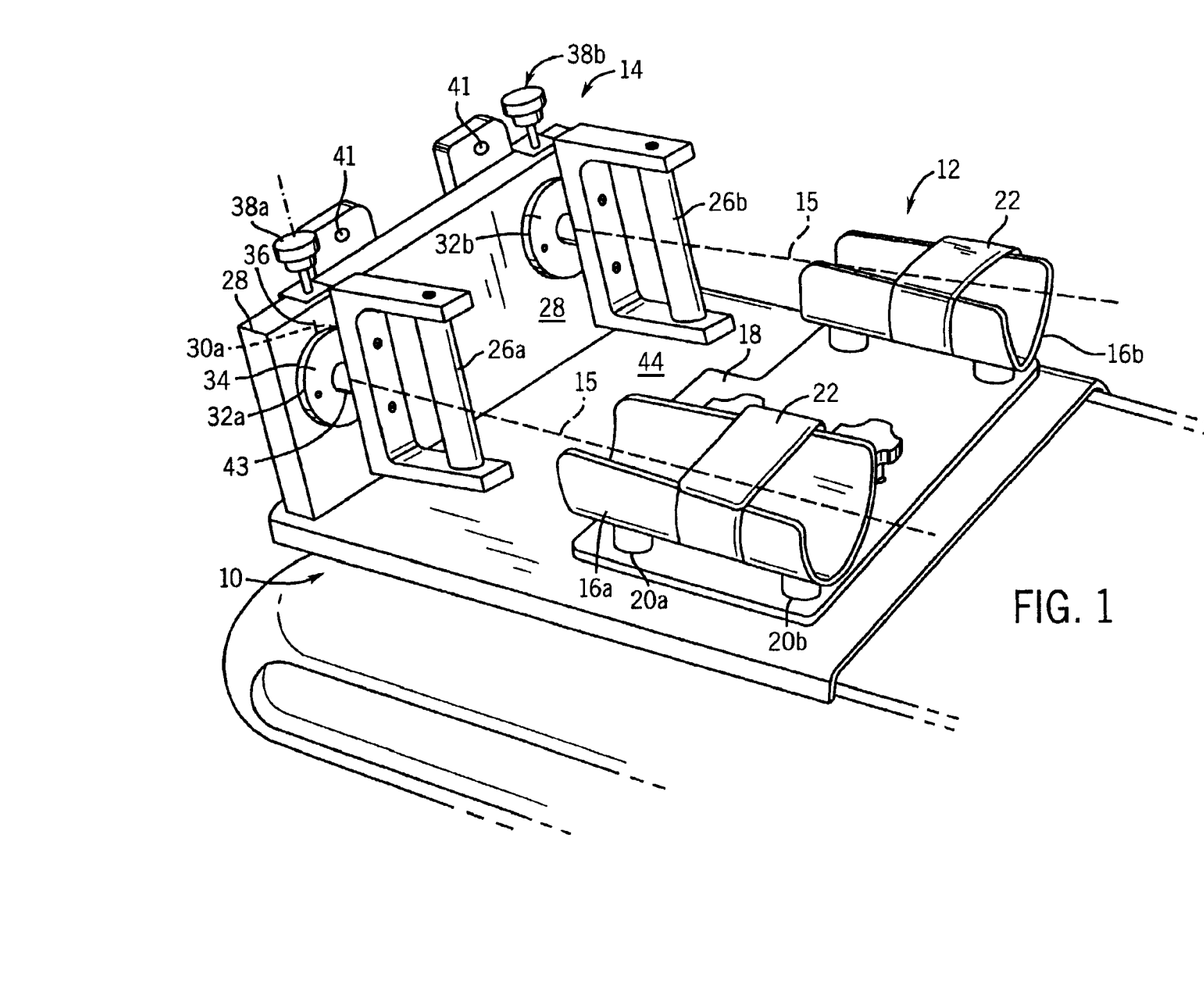
FIG. 1 is a perspective view of a forearm positioning device constructed in accordance with the invention.
Figure 2:
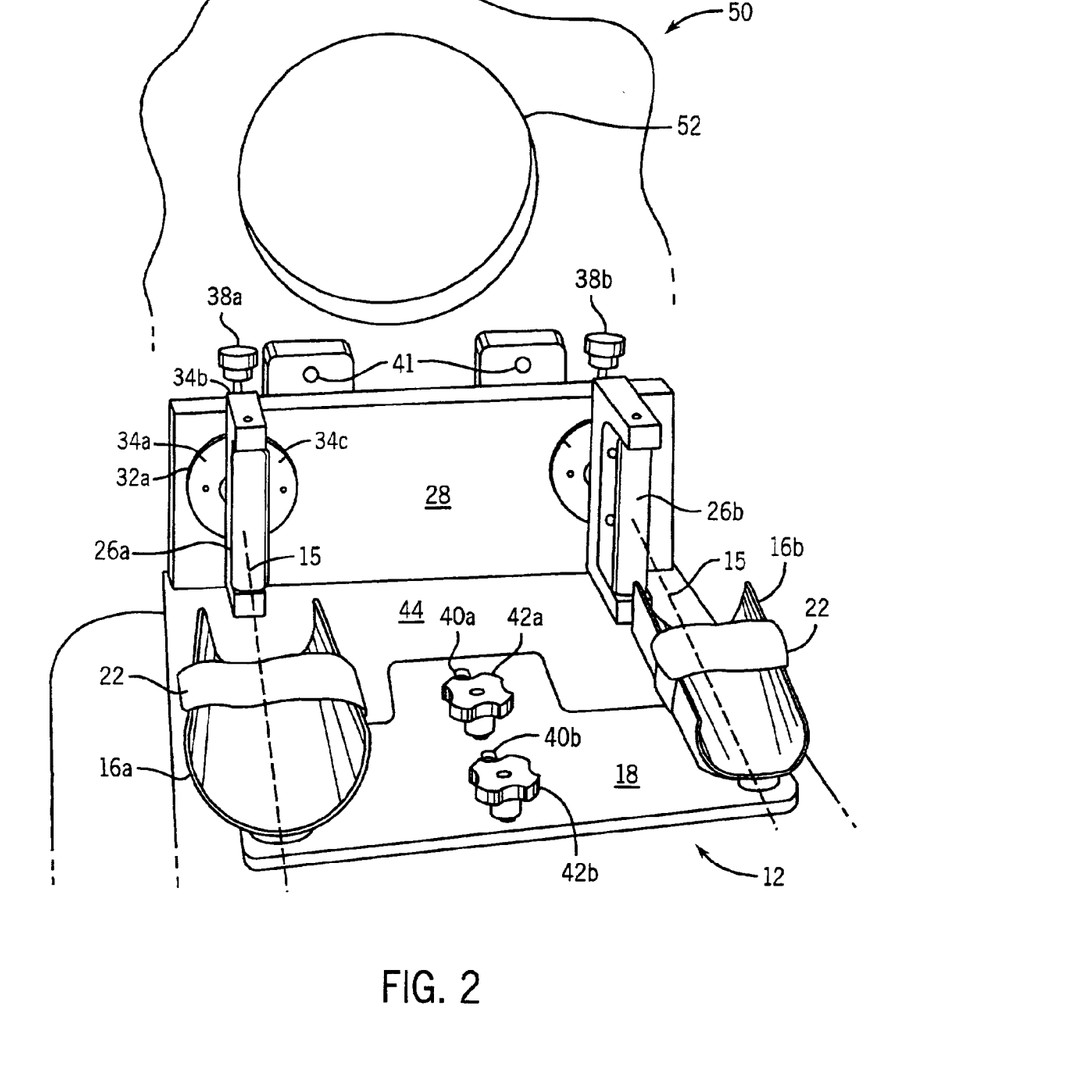
FIG. 2 is a perspective view of the forearm positioning device of FIG. 1, further illustrating the insertion of the device into a computer tomography gantry.

Referring now to the Figures and more particularly to FIG. 1 a forearm positioning device 10 constructed in accordance with the present invention is shown. The forearm positioning device 10 provides a support for maintaining the wrists and forearms of a subject in one or more predefined position for imaging, and is therefore sized and dimensioned for positioning within a scanning or imaging device, and particularly for insertion in a computed tomography (CT) scanner (FIG. 2). The forearm positioning device 10 generally comprises a frame 44 which supports a forearm support assembly 12 and a rotatable handle or grip assembly 14. Each of these assemblies will be described more fully below.

Referring still to FIG. 1 the forearm support assembly 12 comprises first and second forearm support channels 16A and 16B, which are positioned on a mounting plate 18 and aligned in a substantially parallel relationship to each other along parallel longitudinal axes 15. The forearm support channels 16A and 16B are generally U-shaped and are sized and dimensioned to receive the forearms of the subject, and to align and restrain the forearms along their respective axes 15. Each of the forearm support channels 16A and 16B is coupled to the mounting plate 18 by means of mounting posts 20A and 20B, the mounting posts of each of the support channels 16A and 16B being of the same height in order to maintain the forearms of the user 16A and 16B at a substantially equivalent level above a support surface. The mounting posts 20A and 20B can be coupled to the forearm support channels 16A and 16B and the mounting plate 18 by means of threaded fasteners, adhesives or other fastening devices known to those of skill in the art. A forearm restraint 22 which can comprise, for example, a fastening tape, loop and hook fastener, an elastic band or other restraining or locking device, provides a restraint 22 for maintaining the forearm in a stable and stationary position during the scan. The forearm restraint ensures that torque generated at the wrist is produced from the forearm, and not from upper extremity activity.

Referring still to FIG. 1, the grip assembly 14 comprises first and second grip handles 26A and 26B which are coupled to an end plate 28 through a rotatable axle 30A and 30B respectively, each of the grip handles 26A and 26B being substantially aligned along a longitudinal axes 15 with a respective forearm support channel 26A and 26B. The endplate 28 is fastened to the frame 44, and oriented in a plane substantially perpendicular to the mounting plate 18 of the forearm support assembly 12. Each of the axles 30A and 30B is mounted to a faceplate 32A and 32B, respectively. The faceplates 32A and B each include rotational indicators which provide an indication of the degree of rotation of the grip handles 26A and 26B around the longitudinal axes 15 when aligned with a center indicator 36 on the end plate 28. Preferably, an indicator 34A, 34B, and 34C is provided at each of three selected rotation points, as described below. When the grip handles 26A or 26B are rotated to a pre-defined rotation point, a grip lock 38A or B is actuated to lock the axle 30A, 30B in place. The grip lock 38 has an extendable post which is inserted into a mating hole in the axle 30A or 30B to limit further rotation of the grip handle 26A or 26B, as described more fully below.

Referring now to FIG. 2, in the preferred embodiment the grip handles 26A and 26B can be locked at three predefined rotation points around the axes 15: a neutral position; a position of 60° pronation (i.e. with the wrist up); and of 60° supination (i.e. with the wrist down). The grip handles 26A and 26B can be locked in each of these positions by the rotation lock 38. Preferably, a small amount of "play" is provided in the rotation lock 38 such that, even when locked in place, the grip handles 26A and 26B can be rotated within a limited range. Typically, the range of rotation along a lock position is about one degree of rotation around the center point 36. Therefore, when the grip handles 26A and 26B are locked in place, the subject can rotate the hand grips 26A and 26B to provide a stress on the forearm and specifically on the DRUJ for analysis. The lock 38 provides a counter-active force opposing rotation. Referring now also to FIG. 1, a torque cell 43 can be coupled to each of the axles 30A and 30B to provide a signal indicative of the amount of force, and particularly torque that is applied to the hand grips 26A and 26B by the subject, as described below.

Figure 3:
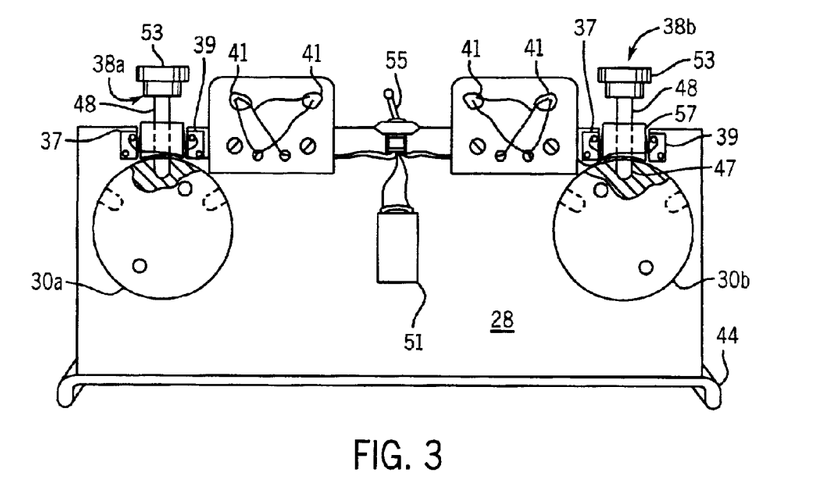
FIG. 3 is a rear view of the endplate of the forearm positioning device of FIG. 1, including a partial drawing of the rotation assembly.
Figures 4A, 4B:
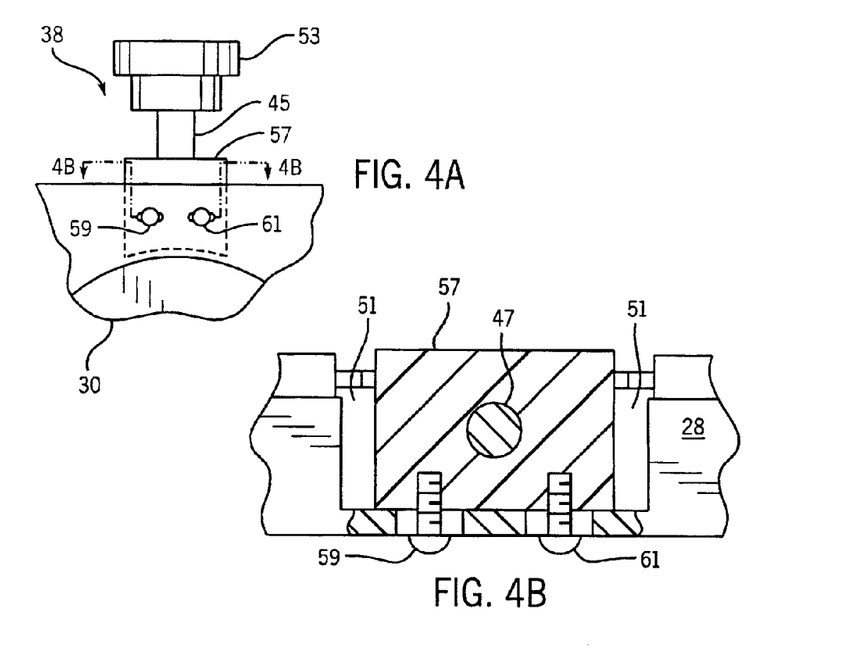
FIG. 4A is a partial view of the rotational lock assembly of FIG. 1.
FIG. 4B is a view of the rotation lock assembly taken above the line 4B—4B of FIG. 4A.

Referring now to FIG. 3, a back view of the end plate 28 is shown. The grip locks 38A and 38B each comprise a handle 53 and locking rod 45 which extends into an aperture 47 (FIG. 4B) in a floating block 57 and then into an aperture 49 in the axle 30A or B. Referring now also to FIGS. 4A and 4B, The floating block 57 is disposed in an aperture 51 formed in the back of the endplate 28, and above the axle 30, and is loosely coupled to the endplate 28 by first and second threaded fasteners 59 and 61. The aperture 51 is sized and dimensioned to allow the floating block 57 to move, wherein rotation of the handle 26 causes the floating block 57 to be driven in the direction of rotation. Preferably, a contact switch 37 is disposed on either side of the floating block 57 wherein, as the hand grips 26A and 26B are rotated, the floating block 57 activates one of the contact switches 37. The contact switches 37 are each electrically coupled to an indicator light, such as a light emitting diode 41, which provides an indication of the direction of rotation applied to the hand grips 26A and 26B. The contact switches 37 and indicator lights 41 are powered by power supply 51 which can be, as shown, a 9 volt dc battery activated by a switch 55. Other types of switches, indicating devices, and power supplies suitable for use in the present invention will be known to those of skill in the art.

Figure 5:
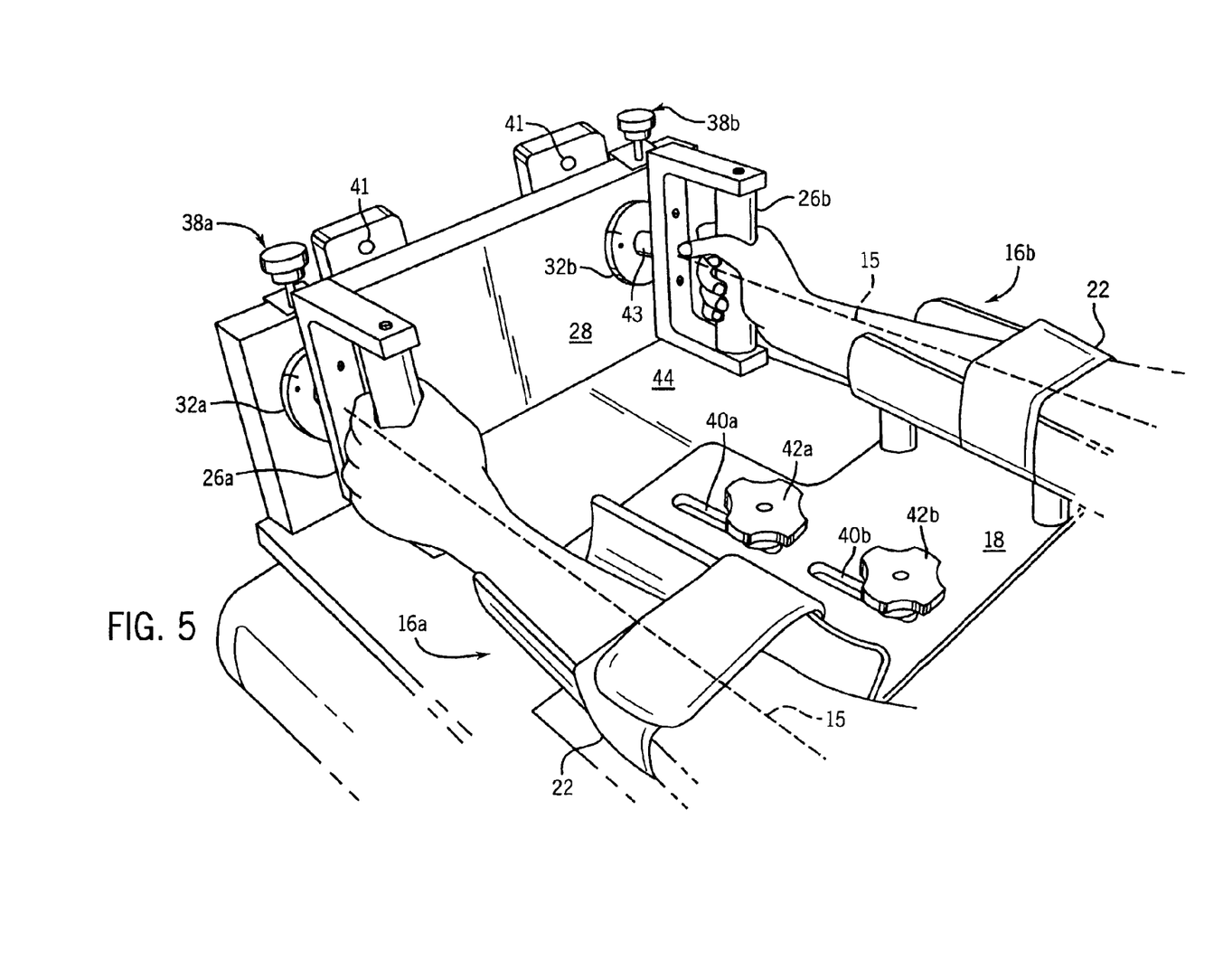
FIG. 5 is a perspective view of the forearm positioning device of FIG. 1 illustrating the wrists of the user in a neutral position.

Referring now to FIG. 5, it can be seen that the forearm support assembly 12 is moveable in a longitudinal direction along the frame 44 of the forearm positioning device 10, thereby allowing the distance between the forearm support channels 16A and 16B and the corresponding hand grips 26A and 26B to be sized and dimensioned to the subject to be examined. One or more grooves 40A and 40B are provided in the mounting plate 18. First and second threaded connectors 42A and 42B are coupled to a mounting threaded receptacle in the frame 44 of the forearm positioning device 10 through the slots 40A and 40B. When the threaded connections 42A and 42B are loosened the mounting plate 18 can be slid along the frame 44 toward the grip handles 24A and 24B or away from the grip handles 24A and 24B. By repositioning the mounting plate 18 on the frame 44, a distance between the forearm support assembly 12 and the grip assembly 14 can be established to fit the forearm positioning device 10 to a particular user. When the mounting plate 18 is positioned at an appropriate distance, the threaded connectors 42A and 42B are tightened to couple the base 18 to the frame 44 in the selected position.

In operation, the subject places each of the right and left forearms in a forearm support channel 16A and 16B respectively. Thereafter, the distance between the forearm support channels 16A and 16B and the hand grips 26A and 26B is adjusted for the subject by adjusting the position of the mounting plate 18 in the slots 40A and 40B as described above. When an appropriate distance is established, each of the forearms can be restrained or locked in place in the forearm support channels 16A and 16B by a restraint 22. In this position, the wrists and forearms of the subjects are aligned along the longitudinal axes 15 and are maintained in a pre-selected, level position for scanning, as can be verified by a laser guide beam 48 associated with a CT scanner 50 (FIG. 2). When the forearms and wrists are appropriately positioned and restrained in the forearm support channels 16A and 16B, the forearm positioning device 10 can be positioned in the gantry 52 of the scanner 50 for scanning or imaging. However, other types of medical examination can also be provided.

Figure 6:
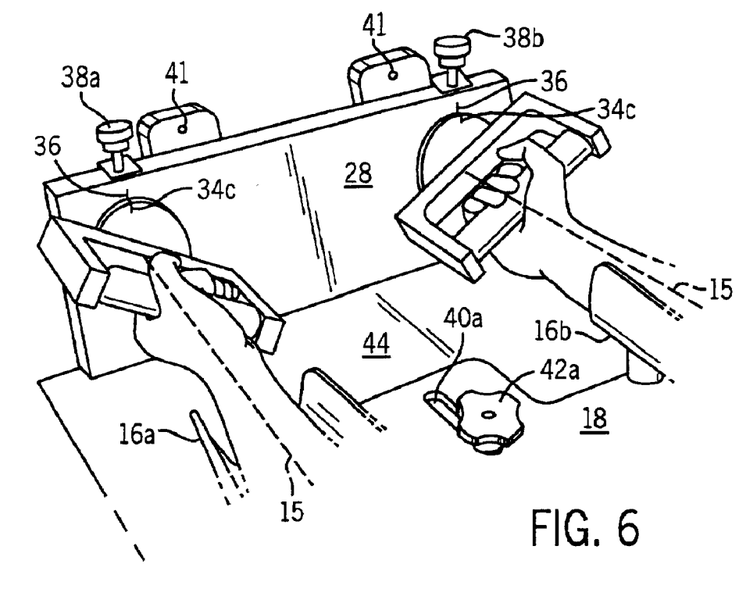
FIG. 6 is a perspective view of the forearm positioning device of FIG. 1 illustrating the wrists of the user in a sixty degree supination position.
Figure 7:
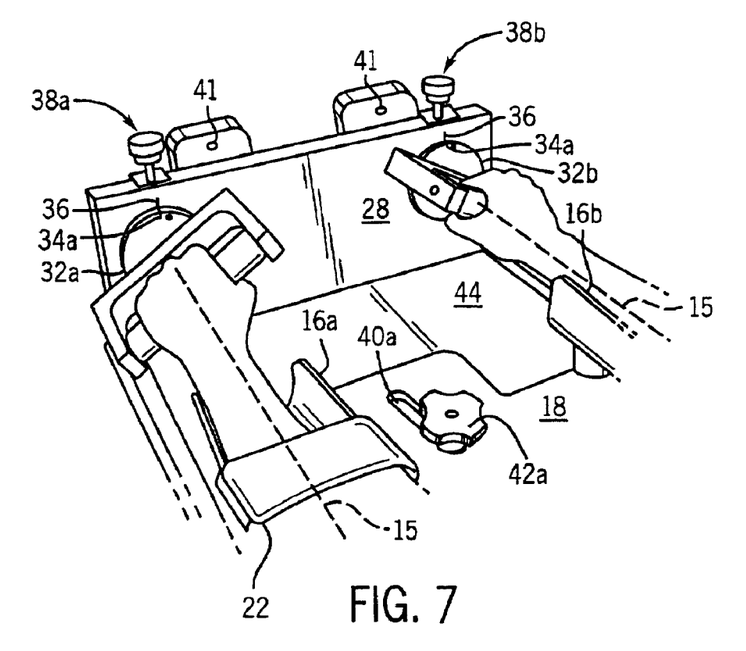
FIG. 7 is a perspective view of the forearm positioning device of FIG. 1 illustrating the wrists of the user in a sixty degree pronation position.

Referring now to FIGS. 5, 6, and 7, the grip handles 26A and 26B are shown as rotated to provide an examination of the forearm and wrists in a plurality of varying rotated and stressed positions. In each of these positions, the forearm positioning device 10 maintains the wrists and forearms in a substantially parallel horizontal plane, and maintains the left and right forearms and wrists in substantially the same rotated position along the longitudinal axes 15 to enable direct comparison of the examination of each wrist. Examination can be provided through CT imaging, wherein the forearm positioning device 19 is positioned in a gantry 52 (FIG. 2) of a CT scanner 50, but can also be accomplished by an analysis of applied torques or through other medical analysis methods.

Referring first to FIG. 5 a subject is shown gripping the hand grips 26A and B as locked in a neutral position 34B by the grip lock 38, providing an image of the wrist and forearm in a stable, unstressed position. Referring now to FIG. 4, the grips 26A and B are shown rotated to the 60° supination position 34C. Here, the right and left wrists are directed upward and a corresponding stress is applied to each of the right and left forearms. Referring now to FIG. 5, the grip handles 26A and 26B are shown locked in the 60° pronation position 34A, such that the right and left wrists of the subject are pointed substantially downward. By examining the wrist and forearm in each of the positions of FIGS. 5–7, instability in the joints can be determined. As described above, in any of these positions, the subject can additionally rotate the hand grips 26A and 26B within a predefined angle of rotation to provide an additional force or torque against the rotation lock 38. Therefore, a stress can be applied to the forearms and wrists of the subject to provide additional information for analysis. The torque cell 43 and an associated metering device 41, such as that shown in FIG. 8, can be provided to measure the amount of torque applied by he forearm and wrist. Furthermore, images of the wrist and forearm in each of the defined positions can be provided by a CT scanner 50 (FIG. 2) or other imaging device.

Figure 8:
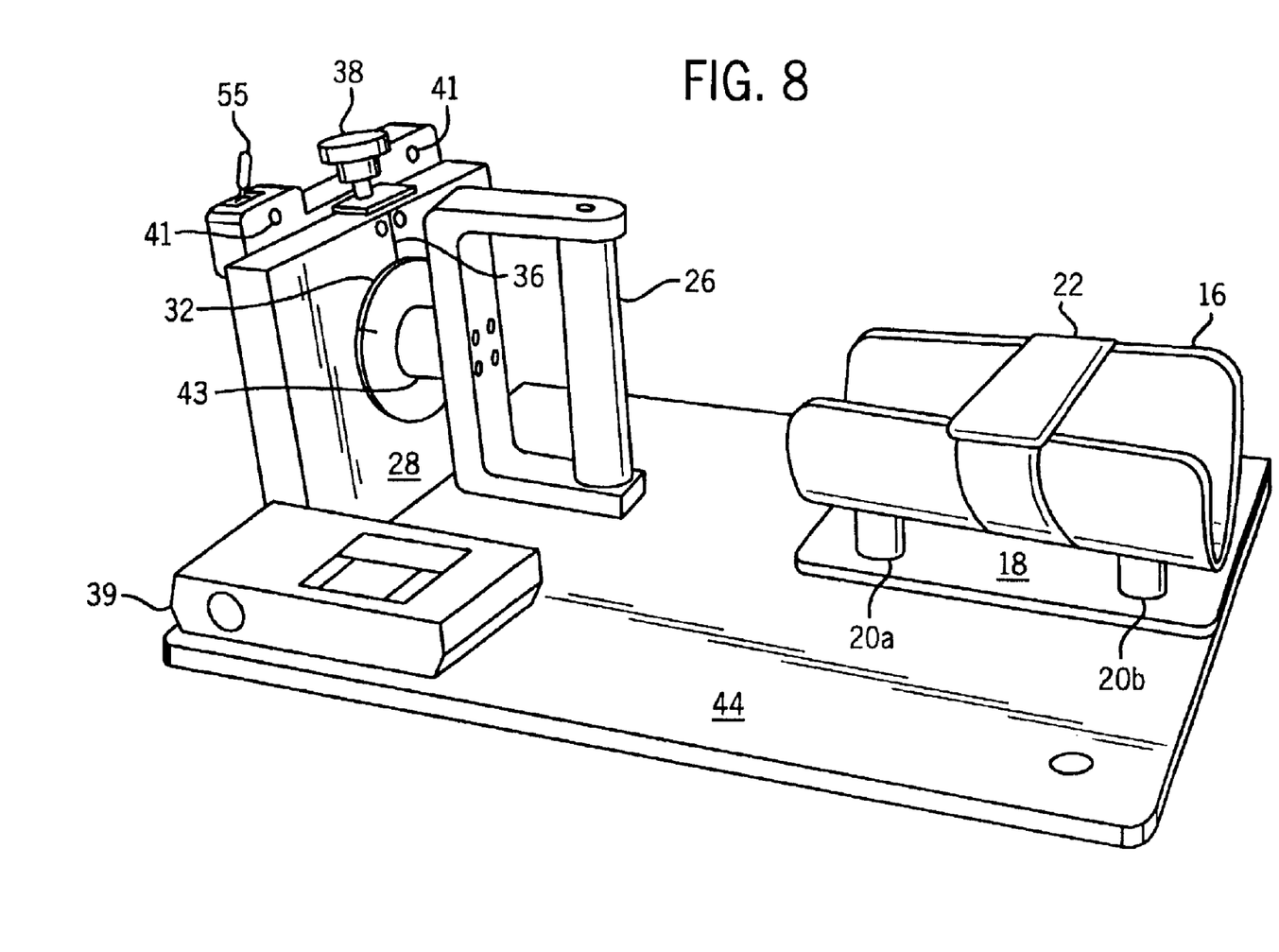
FIG. 8 is a perspective view of a second embodiment of a forearm positioning device constructed in accordance with the present invention.

Referring now to FIG. 8, a forearm positioning device 10 is shown for use in analyzing joint instability based on torque measurement. Here, the forearm positioning device 10 is constructed as described above, including a torque cell 43 and metering device 39. The torque cell 43 can be any of a number of commercially available products, such as the TRT-200 by Transducer Techniques of Temecula, Calif. The associated metering device 39 is also a commercially available product here the PHM-100 transducer indicator, also sold by Transducer Techniques of Temecula, Calif., is a DC conditioner with peakhold and digital readout. The metering device 39 provide a real-time digital read out of applied torque and also stores a maximum value in memory which can be retrieved to obtain a maximum torque value for a given test. The maximum torque value can be reset, and a new value stored for each test. By rotating the handle as described above, and measuring the applied torque at the neutral, 60° supination, and 60° pronation positions, instability in the joint can be determined. The embodiment of FIG. 8 is preferably portable, and can be used both as a clinical evaluation tool, and as a training device for CT scanning. When used as a training device, the forearm positioning device is preferably used in conjunction with a plurality of indicator lights similar to those encountered in a CT scanner, thereby preparing the patient for testing to be applied in a CT scanner.

Although preferred embodiments have been shown and described, it will be apparent to one of ordinary skill in the art that a number of modifications could be made to the method and apparatus described without departing from the scope of the invention. It should be understood, therefore, that the methods and apparatuses described above are only illustrative and do not limit the scope of the invention, and that various modifications could be made by those skilled in the art that would fall under the scope of the invention. To apprise the public of the scope of this invention, the following claims are made:

What is claim is:

1. An apparatus for positioning a forearm of a subject for clinical examination, the combination comprising:
    a frame;
    a support channel coupled to the frame along a longitudinal axis, the support channel being shaped to receive the forearm of the subject;
    a rotatable handle coupled to the frame and positioned at a location relative to the support channel which enables the subject to grip the handle and to rotate the handle substantially around the longitudinal axis to a plurality of fixed angular positions;
    a rotation lock for limiting the rotation of the handle to a selected angle of rotation about a center point;
    first and second contact switches, the first and second contact switches being positioned on either side of the center point; and
    first and second indicator devices, the indicator devices being electrically connected to the first and second contact switches, respectively;
    wherein as the handle is rotated, one of the first and second contact switches is activated, the contact switch activating the indicator device to provide an indication of the direction of rotation.

2. The apparatus as defined in claim 1, further comprising an end plate which supports the rotatable handle and fastens to the frame, and
    a rotation lock mounted to the end plate for locking the handle in at least one of the angular positions to provide a counteractive torque against rotation of the handle by the subject.

3. The apparatus as defined in claim 1, further comprising:
    a mounting plate which supports the support channel and is movably fastened to the frame to enable the distance between the support channel and the rotatable handle to be adjusted to accommodate different subject sizes.

4. The apparatus as defined in claim 3, which includes a fastener that enables the mounting plate to be locked to the frame at a selected distance from the rotatable handle.

5. The apparatus as defined in claim 1, further comprising an end plate therefrom which fastens to the frame and extends upward in a substantially perpendicular relationship to the support channel, the rotatable handle being coupled to the end plate to position the handle at a predefined distance from the support channel.

6. The apparatus as defined in claim 1, wherein the apparatus is sized and dimensioned to be received in a gantry of a computed tomography scanner.

7. The apparatus as defined in claim 1, further comprising a forearm restraint coupled to the support channel.

8. The apparatus as defined in claim 2, wherein the rotation lock is adjustable to a neutral, a sixty degree pronation, and a sixty degree supination position.

9. An apparatus for repeatably positioning and applying a torque to a forearm of a subject for scanning, imaging, or other clinical examination, the apparatus comprising:
    a frame;
    a support channel coupled to the frame, the support channel being sized and dimensioned to receive the forearm of the subject;
    a rotatable handle, the handle being coupled to the frame at a distance from the support channel selected to allow the subject to grip the handle;
    a lock coupled to the rotatable handle, the lock being selectively activated to limit rotation of the rotatable handle to a predefined rotational angle around each of a plurality of selected rotational angles, the lock providing a counteractive force against rotation of the rotatable member by the subject wherein the subject can provide a torque on the handle; and
    a torque cell coupled to the handle, the torque cell providing a signal indicative of the amount of torque applied to the handle.

10. The apparatus as defined in claim 1, further comprising:
    a second support channel; and
    a second rotatable handle, wherein the second support channel and the second handle are disposed in a substantially parallel relationship to the support channel and the handle, the second support channel and the second handle for positioning the forearms of a user in substantially identical position for analysis.

11. The apparatus as defined in claim 1, further comprising:
a torque cell coupled to the rotatable handle, the torque cell providing a measurement of the amount of torque applied by the subject to the handle.

12. The apparatus as defined in claim 11, further comprising a metering device coupled to the torque cell, the metering device providing an indication of the amount of torque applied to the handle.

13. The apparatus as defined in claim 9, further comprising a torque meter electrically connected to the torque cell, the torque meter providing an indicator of the torque applied to the handle.

* * * * *